(12) United States Patent
Makinouchi et al.

(10) Patent No.: US 10,212,758 B2
(45) Date of Patent: Feb. 19, 2019

(54) COMMUNICATION TERMINAL DEVICE, COMMUNICATION SYSTEM, AND COMMUNICATION METHOD USED BY WORKERS UNDERTAKING DANGEROUS OPERATIONS

(71) Applicant: JVC KENWOOD Corporation, Yokohama-shi, Kanagawa (JP)

(72) Inventors: Hideki Makinouchi, Yokohama (JP); Hikaru Sueta, Yokohama (JP); Eiiti Hosono, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 0 days.

(21) Appl. No.: 15/668,952

(22) Filed: Aug. 4, 2017

(65) Prior Publication Data
US 2017/0338886 A1 Nov. 23, 2017

Related U.S. Application Data

(62) Division of application No. 15/041,390, filed on Feb. 11, 2016, now Pat. No. 9,756,666.

(30) Foreign Application Priority Data

Mar. 10, 2015 (JP) .................. 2015-047206
Mar. 10, 2015 (JP) .................. 2015-047207

(51) Int. Cl.
*H04W 76/50* (2018.01)
*H04W 4/02* (2018.01)
(Continued)

(52) U.S. Cl.
CPC .......... *H04W 76/50* (2018.02); *A61B 5/0015* (2013.01); *G06K 7/10297* (2013.01);
(Continued)

(58) Field of Classification Search
CPC ....... H04W 4/023; H04W 4/90; H04W 76/11; H04W 76/50; A61B 5/0015; A61B 2505/01; G06K 7/10297; H04B 7/2693
See application file for complete search history.

(56) References Cited

U.S. PATENT DOCUMENTS

2012/0115542 A1* 5/2012 Griffin .................. H04W 8/205
455/552.1
2014/0282620 A1* 9/2014 Nuovo .............. G06F 17/30867
719/318

FOREIGN PATENT DOCUMENTS

JP 2002271835 A 9/2002
JP 2003-109160 A 4/2003
(Continued)

OTHER PUBLICATIONS

Taichi Ueno et al. "The performance Improvement of a Regional Protection System using a Wireless Network" Feb. 28, 2011, 17 pages.

*Primary Examiner* — Wayne H Cai
(74) *Attorney, Agent, or Firm* — Brundidge & Stanger, P.C.

(57) ABSTRACT

A first communication unit communicates with a first communication terminal device by using a first communication scheme. A second communication unit communicates with a second communication terminal device by using a second communication scheme capable of communication over a longer distance than the first communication scheme. A search instruction communicating unit communicates a search instruction to the second communication terminal device via the second communication unit, the search instruction including an identifier identifying a first communication terminal device, and instructing the second
(Continued)

communication terminal device to search for the first communication terminal device by using the first communication scheme.

2 Claims, 12 Drawing Sheets

(51) Int. Cl.
*H04W 4/90* (2018.01)
*H04W 76/11* (2018.01)
*A61B 5/00* (2006.01)
*G06K 7/10* (2006.01)
*H04B 7/26* (2006.01)

(52) U.S. Cl.
CPC .......... *H04B 7/2693* (2013.01); *H04W 4/023* (2013.01); *H04W 4/90* (2018.02); *H04W 76/11* (2018.02); *A61B 2505/01* (2013.01)

(56) References Cited

FOREIGN PATENT DOCUMENTS

| | | |
|---|---|---|
| JP | 2008113184 A | 5/2008 |
| JP | 2009240530 A | 10/2009 |
| JP | 2013005294 A | 1/2013 |
| WO | 2014021998 A2 | 2/2014 |
| WO | 2015083686 A1 | 11/2015 |

* cited by examiner

COMMUNICATION TERMINAL DEVICE, COMMUNICATION SYSTEM, AND COMMUNICATION METHOD USED BY WORKERS UNDERTAKING DANGEROUS OPERATIONS

CROSS-REFERENCE TO RELATED APPLICATION

This application is based upon and claims the benefit of priority from the prior Japanese Patent Application No. 2015-047206, filed on Mar. 10, 2015, and the prior Japanese Patent Application No.2015-047207, filed on Mar. 10, 2015, the entire contents of each of which are incorporated herein by reference.

BACKGROUND

1. Field of the Invention

The present invention relates to a communication terminal device, communication system, and communication method used by workers who undertake dangerous operations such as fire-fighting operations.

2. Description of the Related Art

A system is proposed in which a biosensor is worn by the body of a firefighter and biological information on the firefighter is transmitted wirelessly to a command center to monitor the safety of the firefighter on a real-time basis. For example, a firefighter is determined to be in a dangerous state if the heart rate of the firefighter is abnormal.

Patent document 1 discloses a mobile terminal for an emergency rescue support system, wherein, when abnormality of the body of a user is detected by referring to a measurement of a biological information sensor, the mobile terminal originates an emergency call to nearby mobile terminals.

Patent Document 1: JP2003-109160

If a worker is located in a place such as a scene of a fire where radio waves from a GPS satellite cannot reach, it may be possible to know that the worker is in a dangerous state by receiving biological information on the worker wirelessly but it is difficult to identify the location of the worker. It is therefore to determine which worker should be sent for a rescue.

SUMMARY

To address the aforementioned issue, a communication terminal device (10) according to an embodiment of the present invention comprises: a second communication unit (132) that communicates with a second communication terminal device (10) by using a second communication scheme capable of communication over a longer distance than a first communication scheme; and a search instruction communicating unit (118a) that communicates a search instruction to the second communication terminal device (10) via the second communication unit (132), the search instruction including an identifier identifying a first communication terminal device (10) that communicates by using the first communication scheme, and instructing the second communication terminal device (10) to search for the first communication terminal device (20) identified by the identifier by using the first communication scheme.

Another embodiment of the present invention also relates to a communication terminal device (10). The communication terminal device (10) comprises: a first communication unit (131) that communicates with a first communication terminal device (20) by using a first communication scheme; and a second communication unit (132) that communicates with a second communication terminal device (10) by using a second communication scheme capable of communication over a longer distance than the first communication scheme; and a searching unit (114) that searches for the first communication terminal device (20) via the first communication unit (131) upon acquiring a search instruction from the second communication terminal device (10) via the second communication unit (132), the search instruction including an identifier identifying the first communication terminal device (20), and instructing the communication terminal device hosting the searching unit to search for the first communication terminal device (20) identified by the identifier by using the first communication scheme.

Still another embodiment of the present invention relates to a communication system (1). The communication system (1) comprises a first communication terminal device (20), a second communication terminal device (10), and a management device (30), wherein the second communication terminal device (10) includes: a second communication unit (132) that communicates with the management device (30) by using a second communication scheme capable of communication over a longer distance than a first communication scheme. The management device (30) includes: a communication unit (331) that communicates by using the second communication scheme, and a search instruction communicating unit (316) that communicates, in response to a trigger signal from the second communication terminal device (10) via the communication unit (331), a search instruction to another second communication terminal device (10) via the communication unit (331), the search instruction including an identifier identifying the first communication terminal device (20) that communicates by using the first communication scheme, and instructing the other second communication terminal device to search for the first communication terminal device (20) identified by the identifier by using the first communication scheme.

Still another embodiment of the present invention relates to a communication method. The method comprises: communicating a search instruction to a second communication terminal device (10) by using a second communication scheme capable of communication over a longer distance than a first communication scheme, the search instruction including an identifier identifying a first communication terminal device (20) that communicates by using the first communication scheme, and instructing the second communication terminal device to search for the first communication terminal device (20) identified by the identifier by using the first communication scheme.

Still another embodiment of the present invention also relates to a communication method. The method is adapted to a communication system (1) including a first communication terminal device (20), a second communication terminal device (10), and a management device (30), the method comprising: using the second communication terminal device (10) to communicate with the management device (30) by using a second communication scheme capable of communication over a longer distance than a first communication scheme. The method further comprises: using the management device (30) to communicate by using the second communication scheme, the management device (30) comprising: a search instruction communicating unit (316) that communicates, in response to a trigger signal from the second communication terminal device (10) by using the second communication scheme, a search instruction to another second communication terminal device (10) by using the second communication scheme, the search instruction including an identifier identifying the first communication terminal device (20) that communicates by using the first communication scheme, and instructing the other second communication terminal device to search for the first communication terminal device (20) identified by the identifier by using the first communication scheme.

Still another embodiment of the present invention relates to a communication terminal device (10). The communication terminal device (10) comprises: a first communication unit (131) that communicates with a first communication terminal device (20) by using a first communication scheme; and a storage unit (12) that stores identifier mapping information that maps a first identifier identifying the first communication terminal device (20) to a second identifier identifying a second communication terminal device (10) that communicates by using a second communication scheme capable of communication over a longer distance than the first communication scheme; a searching unit (114) that searches for the first communication terminal device (20) via the first communication unit (131) and acquires the first identifier of the first communication terminal device (20) detected by the search; and a communication destination determination unit (116) that acquires the second identifier mapped to the first identifier acquired by the searching unit (114), by referring to the identifier mapping information stored in the storage unit (12).

Still another embodiment of the present invention relates to a communication system (1). The communication system (1) comprises a first communication terminal device (20) identified by a first identifier, a second communication terminal device (10) identified by a second identifier, and a management device (30), wherein the first communication terminal device (20) includes a communication unit (231) that communicates with the second communication terminal device (10) by using a first communication scheme. The second communication terminal device (10) includes a first communication unit (131) that communicates with the first communication terminal device (20) by using the first communication scheme; a second communication unit (132) that communicates with the management device (30) by using a second communication scheme capable of communication over a longer distance than the first communication scheme; a searching unit (114) that searches for the first communication terminal device (20) via the first communication unit (131) and acquires the first identifier of the first communication terminal device (20) detected by the search; and a communicating unit (118) that communicates information including the first identifier acquired by the searching unit (114) to the management device (30) via the second communication unit (132). The management device (30) includes: a communication unit (331) that communicates by using the second communication scheme; a storage unit (32) that stores identifier mapping information that maps the first identifier to the second identifier; a communication acquisition unit (313) that receives communication of information including the first identifier from the second communication terminal (10) via the communication unit (331); and a communication destination determination unit (317) that acquires the second identifier mapped to the first identifier acquired by the communication acquisition unit (313) by referring to the identifier mapping information stored in the storage unit (32).

Still another embodiment of the present invention relates to a communication method. The method comprises: searching for a first communication terminal device (20) by using a first communication scheme for communication with the first communication terminal device (20) and acquiring a first identifier of the first communication terminal device (20) detected by the search; and acquiring a second identifier mapped to the first identifier acquired by the search, by referring to identifier mapping information that maps the first identifier for identifying the first communication terminal device (20) to the second identifier for identifying a second communication terminal device (10) that communicates by using a second communication scheme capable of communication over a longer distance than the first communication scheme.

Still another embodiment of the present invention also relates to a communication method. The method is adapted to a communication system (1) including a first communication terminal device (20) identified by a first identifier, a second communication terminal device (10) identified by a second identifier, and a management device (30), the method comprising using the first communication terminal device (20) to communicate with the second communication terminal device (10) by using a first communication scheme. The method further comprises: using the second communication terminal device (10) to communicate with the first communication terminal device (20) by using the first communication scheme; using the second communication terminal device (10) to communicate with the management device (30) by using a second communication scheme capable of communication over a longer distance than the first communication scheme; using the second communication terminal device (10) to search for the first communication terminal device (20) by using the first communication scheme and acquiring the first identifier of the first communication terminal device (20) detected by the search; and using the second communication terminal device (10) to communicate information including the first identifier acquired by the search to the management device (30) by using the second communication scheme. The method further comprises: using the management device (30) to communicate by using the second communication scheme; using the management device (30) to receive the information including the first identifier from the second communication terminal device (10) by using the second communication scheme; and using the management device (30) to acquire the second identifier mapped to the acquired first identifier by referring to mapping information that maps the first identifier to the second identifier.

Optional combinations of the aforementioned constituting elements, and implementations of the invention in the form of methods, apparatuses, systems, recording mediums, and computer programs may also be practiced as additional modes of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which.

DETAILED DESCRIPTION

The invention will now be described by reference to the preferred embodiments. This does not intend to limit the scope of the present invention, but to exemplify the invention.

Embodiments of the present invention relate to a dangerous operation support system for supporting firefighting operations of a firefighting team formed by multiple firefighters. In the following description, a firefighting operation is taken by as an example. A firefighting operation is given as an example of dangerous operations and the system is applicable to dangerous operations in general in which multiple workers cooperate. For example, the system is applicable to rescue operations or recovery operations undertaken in the event of a natural disaster such as an earthquake or landslide. The system is also applicable to operations in dangerous places such as sites of mine development.

Figure 1:
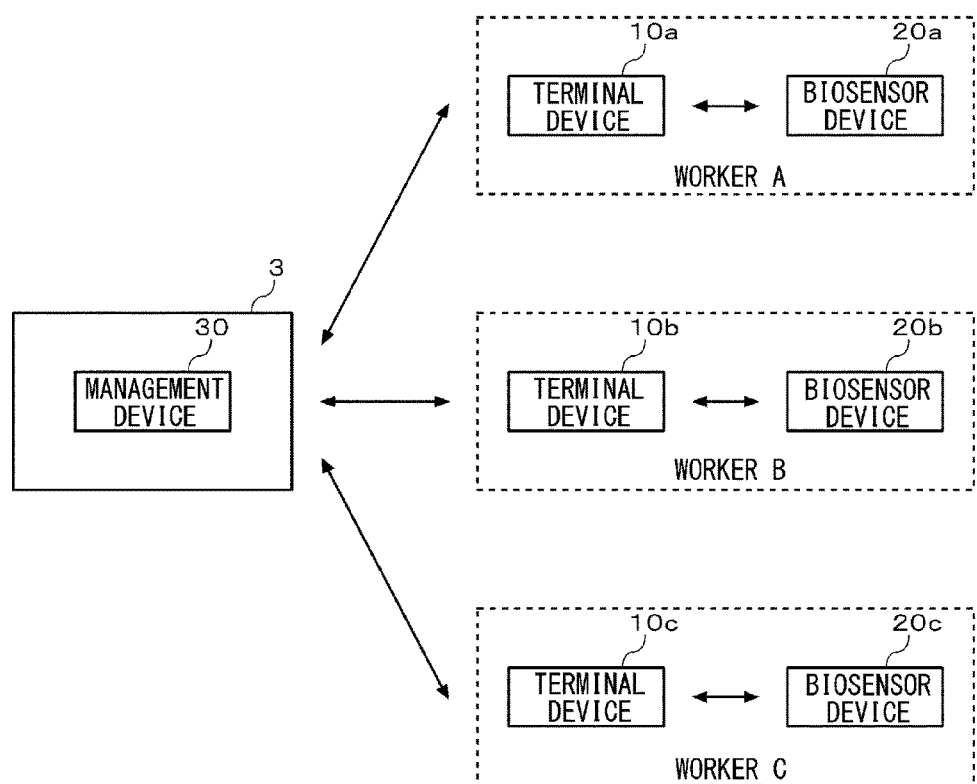
FIG. 1 shows the configuration of the dangerous operation support system according to the embodiments of the present invention.

FIG. 1 shows the configuration of a dangerous operation support system 1 according to the embodiments of the present invention. The dangerous operation support system 1 includes a management device 30 installed at a command center 3, a biosensor device 20 worn by each worker, and a terminal device 10 held or carried by each worker. In this specification, a case of three workers is taken as an example.

The biosensor device 20 is worn by the body of the worker and detects biological information such as heart rate, body temperature, and posture. The biosensor device 20 is available in various types including a type glued to the body by a gel pad, a type wound around the arm or leg by a band, a type attached inside a clothing. Near field communication is established between the biosensor device 20 and the terminal device 10. In this specification, an example in which Bluetooth (registered trademark) is used as near field communication is described. Near field communication other than Bluetooth (registered trademark), such as wireless LAN, infrared communication, may be used for near field communication.

A simplified mobile wireless device for business wireless communication is used as the terminal device 10. The management device 30 is installed at a place such as a fire station or command van that serves as the command center 3. The management device 30 may be implemented by a PC connected to the base station radio device for business wireless communication. Instead of using business wireless communication, an ordinary cell phone network may be used. In this case, the terminal device 10 may be implemented by an ordinary mobile terminal device such as a smartphone, feature phone, etc. The management device 30 may be implemented by a PC connected to the IP network. In the description below, business wireless communication is assumed to be used.

Figure 2:
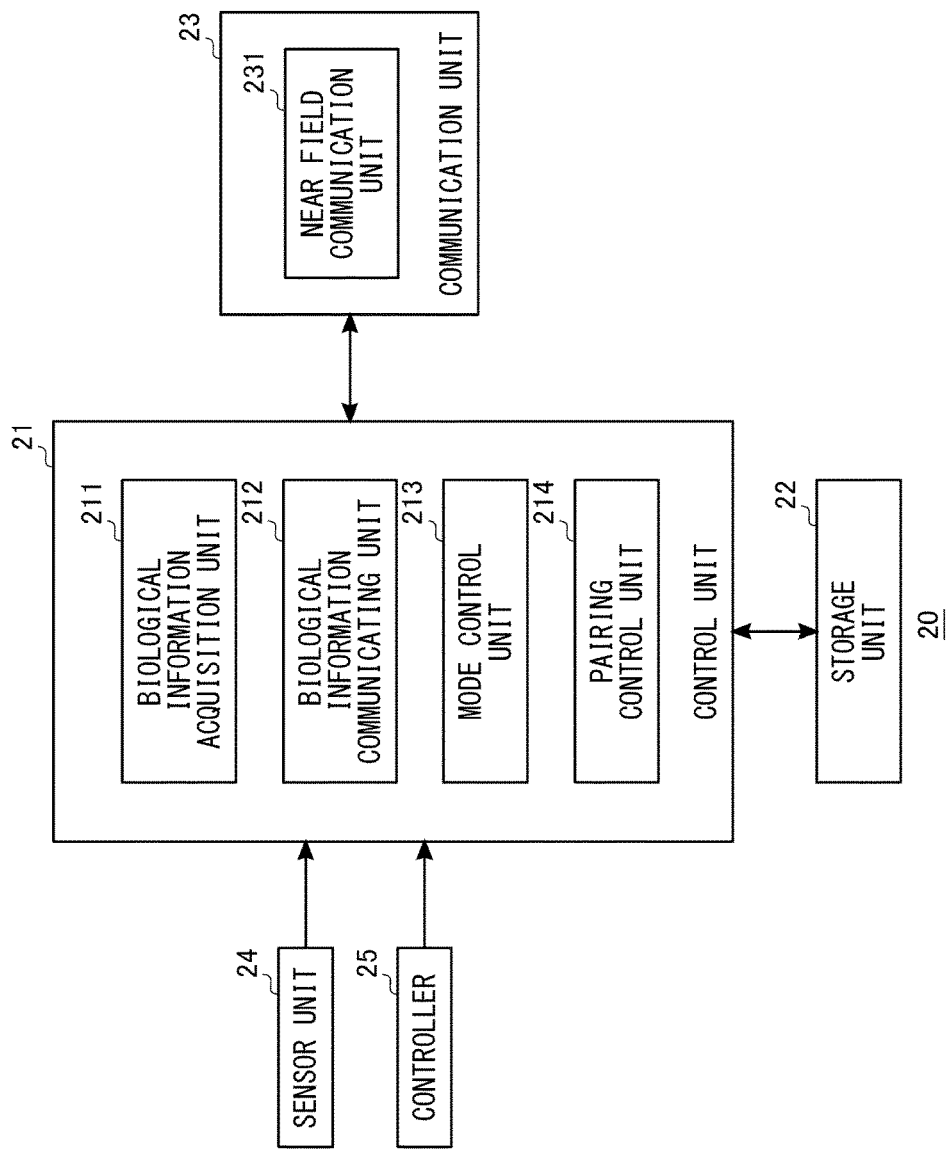
FIG. 2 shows the configuration of the biosensor device according to the embodiments.

FIG. 2 shows the configuration of the biosensor device 20 according to the embodiments. The biosensor device 20 includes a control unit 21, a storage unit 22, a communication unit 23, a sensor unit 24, and a controller 25. The control unit 21 includes a biological information acquisition unit 211, a biological information communicating unit 212, a mode control unit 213, and a pairing management unit 214. The functions of the control unit 21 are implemented by the coordination of hardware resources and software resources, or hardware resources alone. A processor, ROM, RAM, and other LSIs can be used as hardware resources. Programs such as firmware can be used as software resources. FIG. 2 depicts only those function blocks of the control unit 21 related to the process of interest in the embodiments.

The storage unit 22 includes a storage medium such as a nonvolatile semiconductor memory. The communication unit 23 includes a near field communication unit 231. Medium or long distance wireless communication capabilities of a business wireless communication system, a cell phone network, etc. are not provided. The sensor unit 24 includes a heart rate sensor, a body temperature sensor, a three-axis acceleration sensor or the like to detect the heat rate, body temperature, posture or the like of the worker wearing the device. The sensor unit 24 outputs the detected biological information to the control unit 21.

The biological information acquisition unit 211 acquires the detected biological information from the sensor unit 24. The biological information communicating unit 212 periodically (e.g., at the intervals of several seconds) communicates the acquired biological information to the terminal device 10 paired with the biosensor device 20 via the near field communication unit 231. A description of the mode control unit 213 and the pairing management unit 214 will be given later. The configuration of the biosensor device 20 shown in FIG. 2 is common to Embodiments 1 and 2 described below.

Embodiment 1

Figure 3:
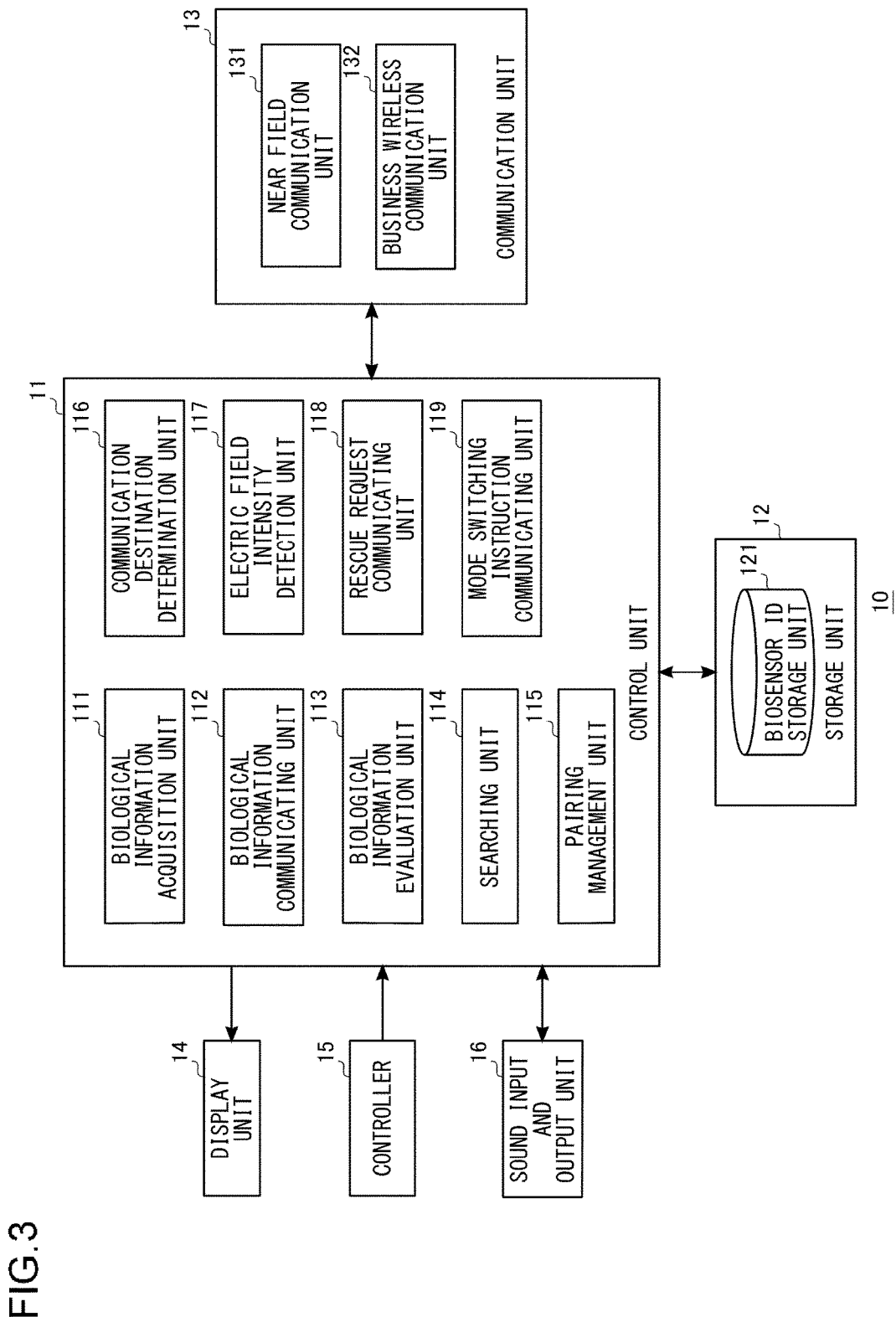
FIG. 3 shows the configuration of the terminal device according to Embodiment 1.

FIG. 3 shows the configuration of the terminal device 10 according to Embodiment 1. The terminal device 10 includes a control unit 11, a storage unit 12, a communication unit 13, a display unit 14, a controller 15, and a sound input and output unit 16. The control unit 11 includes a biological information acquisition unit 111, a biological information communicating unit 112, a biological information evaluation unit 113, a searching unit 114, a pairing management unit 115, a communication destination determination unit 116, an electric field detection unit 117, a rescue request communicating unit 118, and a mode switching instruction communicating unit 119. The functions of the control unit 21 are also implemented by the coordination of hardware resources and software resources, or hardware resources alone. FIG. 3 depicts only those function blocks of the control unit 11 related to the process of interest in Embodiment 1.

The storage unit 12 includes a storage medium such as a nonvolatile semiconductor memory. The storage unit 12 includes a biosensor ID storage unit 121. FIG. 3 also depicts only those function blocks of the storage unit 12 related to the process of interest in Embodiment 1. The biosensor ID storage unit 121 stores identification information on multiple biosensor devices 20 respectively worn by multiple workers belonging to a team undertaking a disaster-relief operation in cooperation with each other. The sound input and output unit 16 includes a microphone and a speaker.

The communication unit 13 includes a near field communication unit 131 and a business wireless communication unit 132. The near field communication unit 131 is used for communication with the biosensor device 20 and the business wireless communication unit 132 is used for communication with the management device 30 or another terminal device 10.

Figure 4:
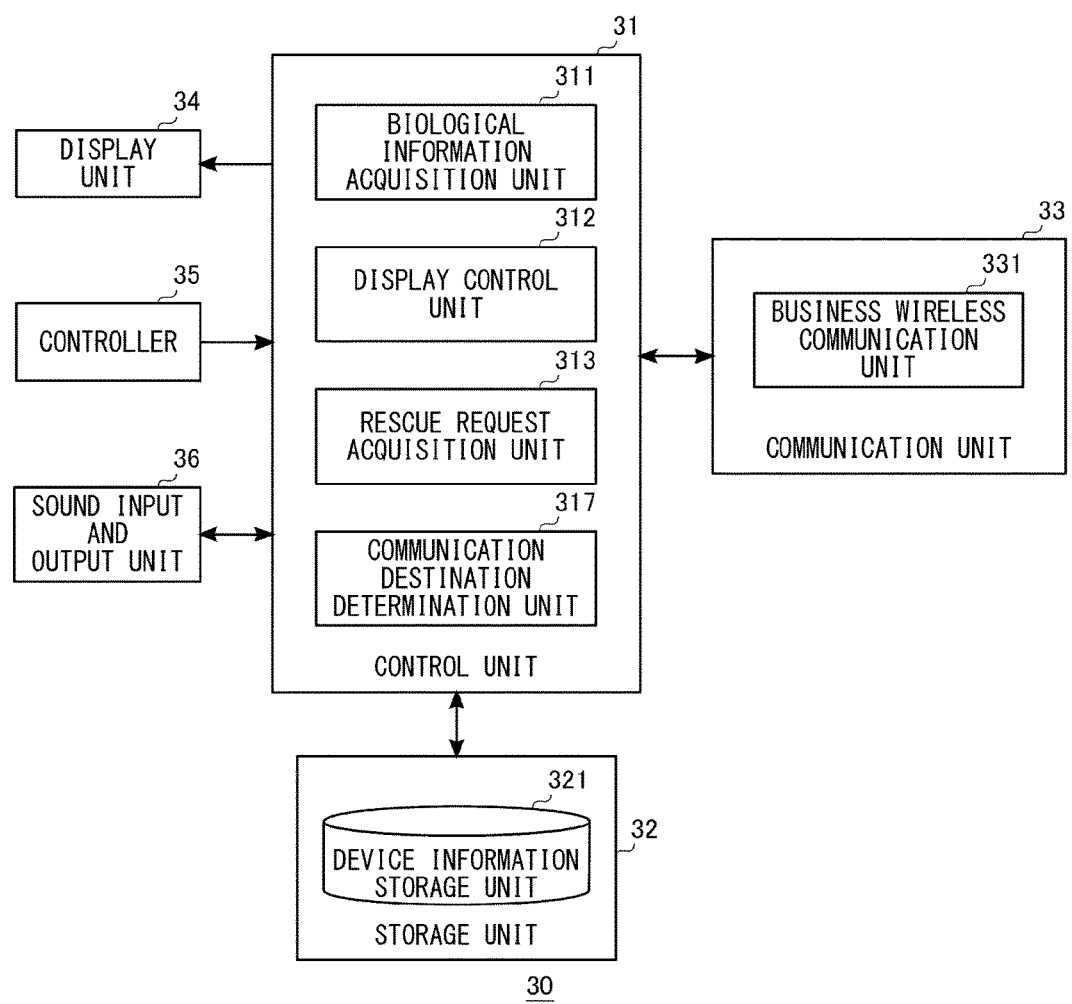
FIG. 4 shows the configuration of the management device according to Embodiment 1.

FIG. 4 shows the configuration of the management device 30 according to Embodiment 1. The management device 30 includes a control unit 31, a storage unit 32, a communication unit 33, a display unit 34, a controller 35, and a sound input and output unit 36. The control unit 31 includes a biological information acquisition unit 311, a display control unit 312, a rescue request acquisition unit 313, and a communication destination determination unit 317. The functions of the control unit 31 are also implemented by the coordination of hardware resources and software resources, or hardware resources alone. FIG. 4 also depicts only those function blocks of the control unit 31 related to the process of interest in Embodiment 1.

The storage unit 32 includes a storage medium such as a nonvolatile semiconductor memory. The storage unit 32 includes a device information storage unit 321. FIG. 4 also depicts only those function blocks of the storage unit 32 related to the process of interest in Embodiment 1. The device information storage unit 321 stores the name of a worker, identification information on the terminal device 10 carried by the worker, and identification information on the biosensor device 20 worn by the worker, mapping the information to each other. The terminal device 10 and the biosensor device 20 may be permanently assigned to each worker for use. Alternatively, the terminal device 10 and the biosensor device 20 used may be dynamically changed. The sound input and output unit 36 includes a microphone and a speaker.

The operation of the terminal device 10, the biosensor device 20, and the management device 30 will be described below in specific details with reference to FIGS. 5-8. First, a description will be given of the process performed before a worker arrives at a scene of a disaster. Each worker should pair the biosensor device 20 worn by the worker, a slave module of Bluetooth (registered trademark) (hereinafter, simply referred to as a slave module), and the terminal device 10 that the worker carries with him or her, a master module of Bluetooth (registered trademark) (hereinafter, simply referred to as a master module). The biosensor device 20 is in either of two modes including the normal mode in which the device does not respond to a pairing search from the master and the pairing mode in which the device responds to a pairing search from the master. In the normal mode, the existence of the device is not disclosed to a search from the master module to protect privacy and prevent unauthorized access.

Figure 5:
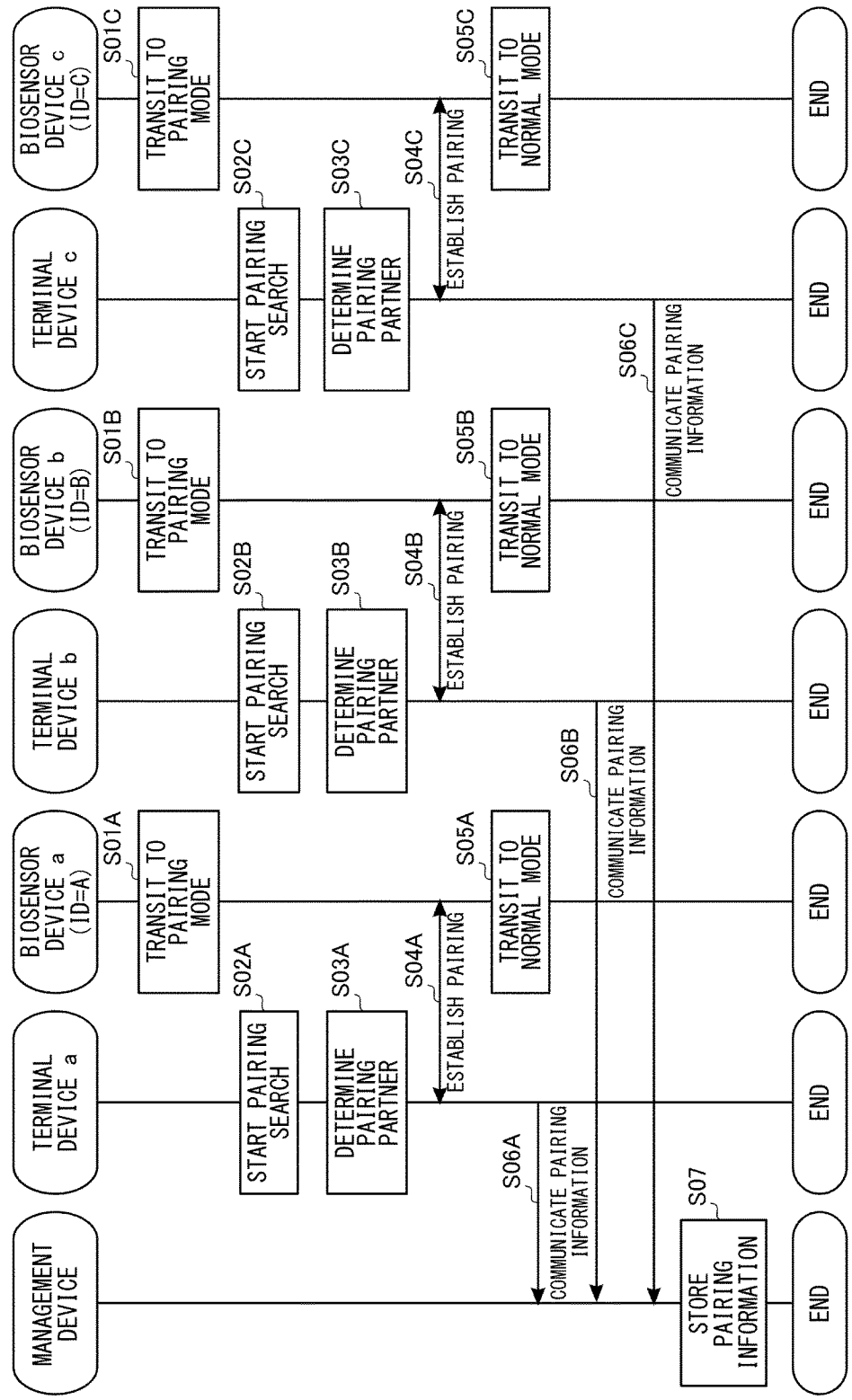
FIG. 5 is a flowchart illustrating the pairing process performed in a preparatory stage.

FIG. 5 is a flowchart illustrating the pairing process in the preparatory stage. When worker A uses the controller 25 of the biosensor device 20a to designate a transition to the pairing mode, the mode control unit 213 of the biosensor device 20 causes the host device to make a transition from the normal mode to the pairing mode (S01A). When worker A uses the controller 15 of the terminal device 10a to request a pairing search, the searching unit 114 starts searching for a device capable of pairing connection (S02A). The pairing search detects a device capable of pairing connection and located within the range of near field communication. Only those devices that are in the pairing mode are detected, and devices in the normal mode are not detected.

When worker A uses the controller 15 of the terminal device 10a to select the biosensor device 20a, the pairing management unit 115 determines the selected biosensor device 20a as the pairing device (S03A) and establishes pairing with the biosensor device 20a (S04A). Similarly, the pairing management unit 214 of the biosensor device 20a establishes pairing with the terminal device 10a (S04A). When pairing is established, the mode control unit 213 of the biosensor device 20a causes the host device to make a transition from the pairing mode to the normal mode (S05A). When pairing is established, the pairing management unit 115 of the terminal device 10a communicates, to the management device 30, pairing information including the identification information on the terminal device 10a, the identification information on the biosensor device 20a, and the name of the worker (S06A).

The identification information on the pairing device is stored in the storage unit 12 of the terminal device 10a and the storage unit 22 of the biosensor device 20a. This allows the terminal device 10a and the biosensor device 20a to establish pairing automatically when they are turned on subsequently. Like worker A, worker B and worker C also pair the terminal devices 10b and 10c with the biosensor devices 20b and 20c, respectively. The control unit 31 of the management device 30 acquires pairing information from the terminal devices 10a, 10b, and 10c and stores the acquired information in the device information storage unit 321 (S07). If the terminal device 10 and the biosensor device 20 are permanently assigned to each worker for use, the processes in step S06 and S07 are omitted.

A description will now be given of the process performed during a firefighting operation at a scene of a disaster. The biosensor devices 20a-20c are worn by the bodies of workers A-C. The workers A-C hold the terminal devices 10a-10c, respectively. The biosensor devices 20a-20c and the terminal devices 10a-10c are respectively paired by near field communication. The terminal devices 10a-10c are master modules and the biosensor devices 20a-20c are slave modules.

Figure 6:
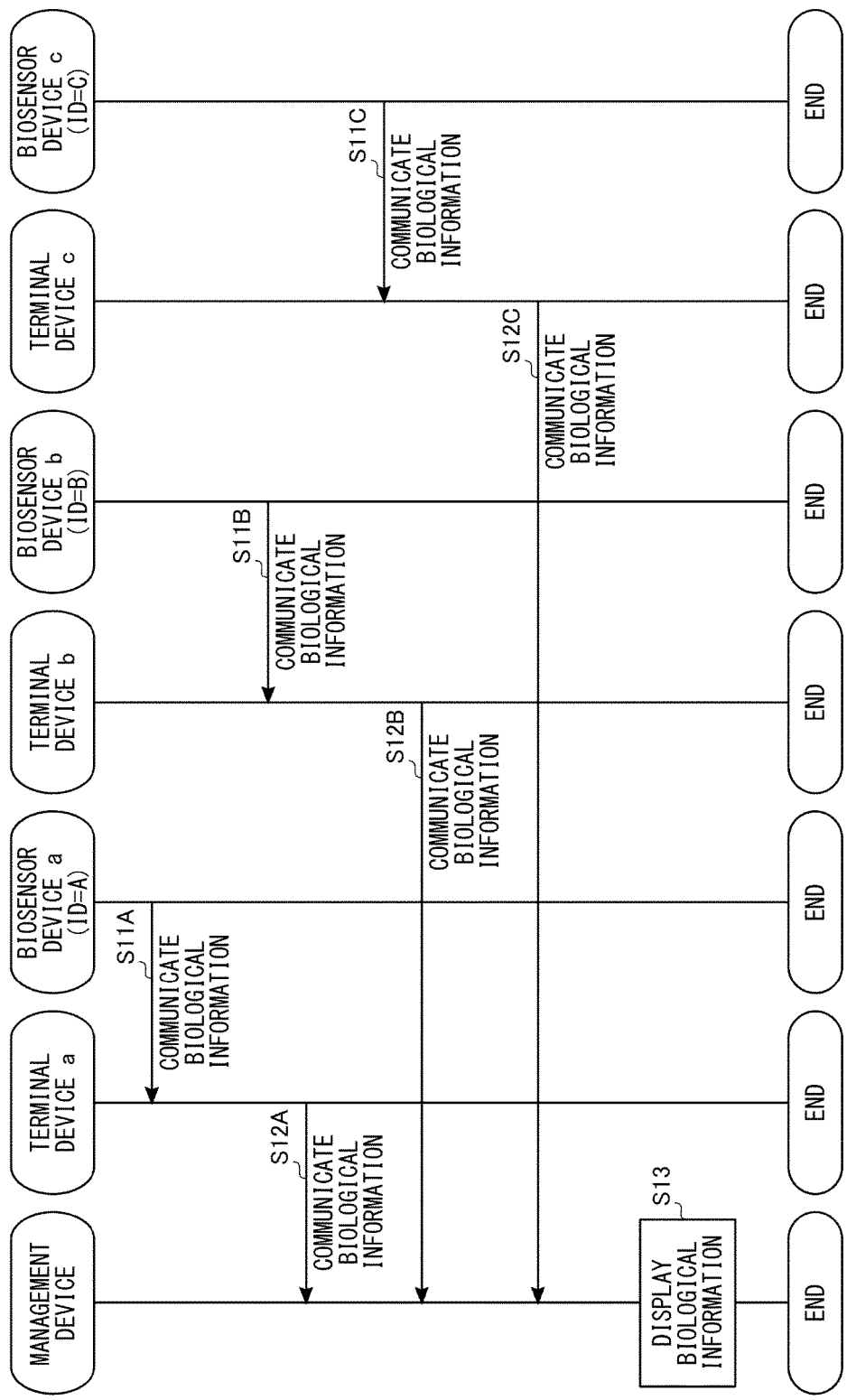
FIG. 6 is a flowchart showing the flow of the basic process in the dangerous operation support system.

FIG. 6 is a flowchart showing the flow of the basic process in the dangerous operation support system 1. The biological information acquisition unit 211 of the biosensor device 20a acquires biological information on worker A from the sensor unit 24. The biological information communicating unit 212 communicates the acquired biological information to the terminal device 10a by near field communication (S11A).

The biological information acquisition unit 111 of the terminal device 10a paired with the biosensor device 20a acquires the biological information from the biosensor device 20a by near field communication. The biological information communicating unit 112 communicates the biological information to the management device 30 of the command center 3 by business wireless communication (S12A). The biological information on workers B and C are similarly communicated to the management device 30 of the command center 3.

The biological information acquisition unit 311 of the management device 30 acquires the biological information on workers A-C by business wireless communication. The display control unit 312 causes the display unit 34 to display the acquired biological information on workers A-C (S13). The commander at the command center 3 monitors the biological information on workers A-C displayed on the display unit 34 and know the states of workers A-C. The commander sends commands based on the states of workers A-C thus known. For example, if the heart rate of worker A shows an abnormal increase, the commander directs worker A to stop the firefighting operation and pull out. For example, the direction is given by outputting sound from the sound input and output unit 36 to the terminal device 10a carried by firefighter A by business wireless communication.

Figure 7:
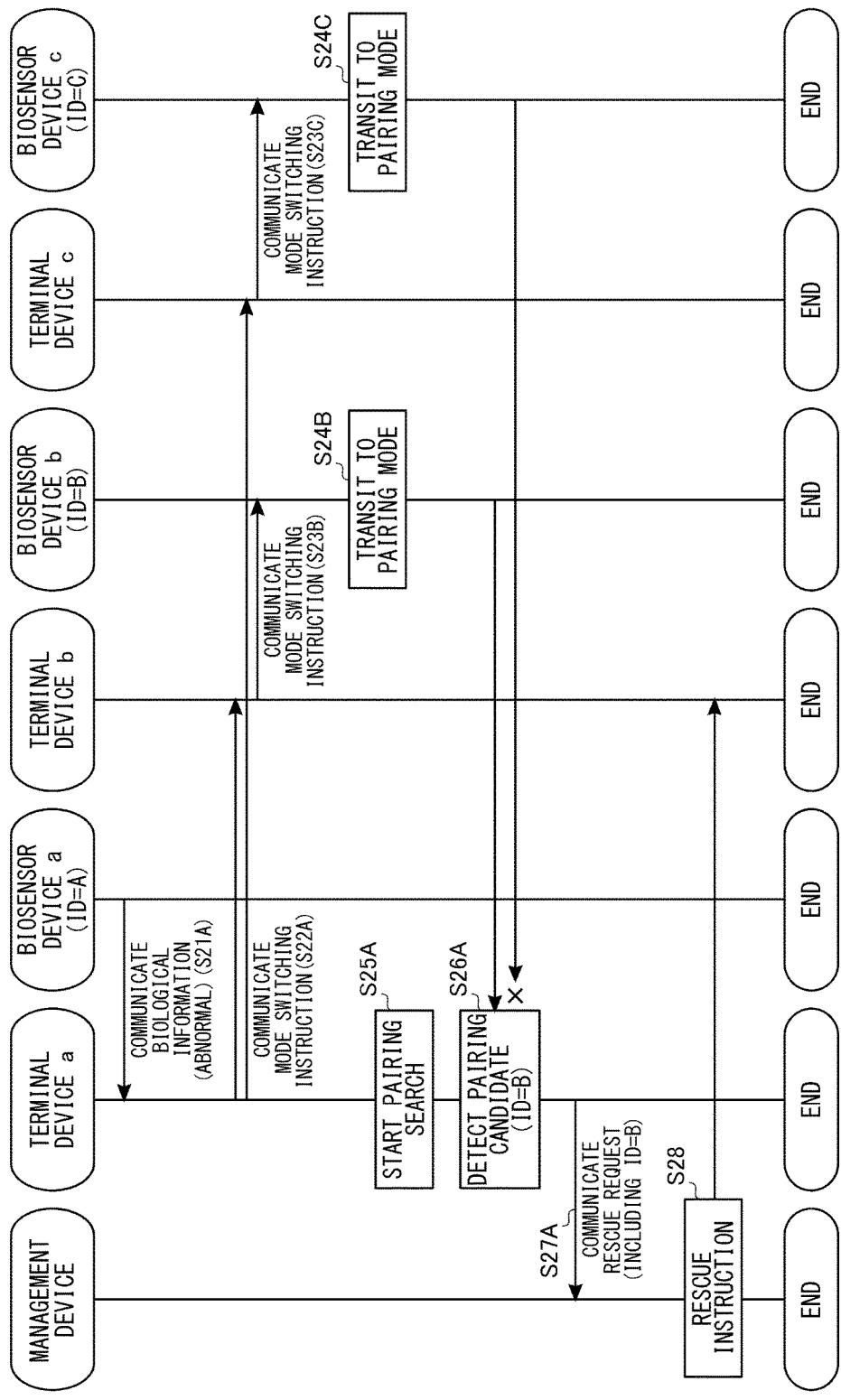
FIG. 7 is a flowchart illustrating a method of requesting a rescue by using the dangerous operation support system according to Embodiment 1.

FIG. 7 is a flowchart illustrating a method of requesting a rescue by using the dangerous operation support system 1 according to Embodiment 1. The biological information acquisition unit 211 of the biosensor device 20a acquires biological information on worker A from the sensor unit 24. The biological information communicating unit 212 communicates the acquired biological information to the terminal device 10a by near field communication (S21A).

The biological information acquisition unit 111 of the terminal device 10a paired with the biosensor device 20a acquires the biological information on worker A from the biosensor device 20a by near field communication. The biological information evaluation unit 113 determines whether the acquired biological information on worker A is normal. For example, the biological information evaluation unit 113 determines whether the heart rate is accommodated within the normal range. If it is not accommodated in the normal range, a determination of abnormality is yielded. If the biological information is abnormal, it is estimated that worker A is in a dangerous state.

The biological information may be evaluated in the biosensor device 20a. In this case, flag information indicating normality/abnormality is appended to the biological information transmitted from the biosensor device 20a. If biological information is evaluated in the biosensor device 20a, the biological information evaluation unit 113 of the terminal device 10a can be omitted.

If the biological information on worker A is determined to be abnormal, the mode switching instruction communicating unit 119 of the terminal device 10a communicates a mode switching instruction to the other terminal devices 10b and 10c by business wireless communication to direct the other terminal devices 10b and 10c to switch the mode of the biosensor devices 20b and 20c to the pairing mode (S22A). When the mode switching instruction communicating unit 119 of the terminal device 10b acquires the mode switching instruction from the terminal device 10a by business wireless communication, the mode switching instruction communicating unit 119 communicates the mode switching instruction to the biosensor device 20b by near field communication (S23B). When the mode control unit 213 of the biosensor device 20b acquires the mode switching instruction from the terminal device 10b by near field communication, the mode control unit 213 causes the biosensor device 20b to make a transition from the normal mode to the pairing mode (S24B).

The terminal device 10c and the biosensor device 20c operate similarly. This allows the biosensor devices 20b and 20c to be detected by the terminal device 10a. If the devices are configured to return a response to a pairing search from other devices in the normal mode as well, the processes in steps S22A, S23B, S23C, S24B, and S24C are omitted.

The searching unit 114 of the terminal device 10a starts a pairing search to search for a device connectable by near field communication (S25A). As a result of the search, the biosensor device 20b worn by worker B at a location capable of near field communication with the terminal device 10a held by worker A, i.e., near the terminal device 10a, is detected as a pairing candidate. Meanwhile, the biosensor device 20c worn by worker C at a location incapable of near field communication with the terminal device 10a held by worker A, i.e., not near the terminal device 10a, is not detected as a pairing candidate (S26A). For example, given that Class 2 Bluetooth (registered trademark) is used, communication is disabled at a distance of about 10 m or more. The searching unit 114 acquires the identification information on the biosensor device 20b identified by the search from the biosensor device 20b via the near field communication unit 131 (S26A).

The rescue request communicating unit 118 communicates, to the management device 30, a rescue request including information indicating that worker A is in a dangerous state and the information acquired by the searching unit 114 (the identification information (ID=B) of the biosensor device 20b, in the case of FIG. 3) by business wireless communication.

The rescue request acquisition unit 313 of the management device 30 acquires the rescue request from the terminal device 10a by business wireless communication. The communication destination determination unit 317 acquires the identification information on the terminal device 10 mapped to the identification information on the biosensor device 20 acquired by the rescue request acquisition unit 313, based on the device information stored in the device information storage unit 321. The display control unit 312 causes the display unit 34 to display that worker A is in a dangerous state and that worker B is nearby. The display control unit 312 also causes the display unit 34 to display the device information on worker B acquired from the device information storage unit 321. The commander viewing the screen on which these items of information are shown tells worker B that worker A in a dangerous state is nearby and directs worker B to rescue worker A. For example, the commander sends sound to the terminal device 10b by business wireless communication (S28).

If multiple biosensor devices 20 connectable to the terminal device 10a by near field communication are detected as a result of the pairing search in step S26A above, the electric field detection unit 117 detects the radio field intensity of response signals transmitted from the connectable biosensor devices 20. It is estimated that the higher the radio field intensity, the closer to the terminal device 10a. If the devices are configured to return a response to a pairing search from other devices in the normal mode as well, the processes in steps S22A, S23B, S23C, S24B, and S24C are omitted. In this case, the biosensor device 20a worn by the worker himself is excluded from the candidates of destination of communication.

Alternatively, the rescue request communicating unit 118 may communicate information on destinations of sending a rescue request by communicating the identification information on all the biosensor devices 20 detected as a result of the pairing search and the radio field intensity of the respective biosensor devices 20. The commander at the command center 3 can determine the destination to send a rescue request based on the information on radio field intensity.

As described above, the terminal device 10a according to this embodiment performs the processes based on the radio field intensity in near field communication from the respective biosensor devices 20 instead of the radio field intensity in business wireless communication from the respective terminal devices 10. This is because the output voltage in business wireless communication or cell phone communication is higher than that of near field communication so that it is difficult to estimate the distance from other workers located at the same scene based on the radio field intensity. If a scheme of communication routed by a base station or a relay station is employed for business wireless communication or cell phone communication, the radio field intensity detected will represent the intensity of radio field from the base station or the relay station, which is another reason why it is impossible to estimate the distance from the respective terminal devices 10 in communication.

If multiple biosensor devices 20 connectable to the terminal device 10a by near field communication are detected as a result of the pairing search in step S26A above, the pairing management unit 115 of the terminal device 10a may establish pairing with all the biosensor devices 20 detected. If the system is designed to enable only one-to-one pairing, the terminal device 10a and the detected biosensor devices 20 cancel the pairing established previously and establish pairing between the terminal device 10a and the detected biosensor device 20.

The biological information acquisition unit 111 of the terminal device 10a acquires biological information from the biosensor device 20 newly paired with the terminal device 10a. The biological information evaluation unit 113 determines whether the value indicated by the biological information is in a dangerous range. If the value indicated by the biological information is in a dangerous range, the terminal device 10 held by the worker wearing the biosensor device 20 is excluded from the destinations of sending a rescue request. In other words, the rescue request communicating unit 118 excludes the terminal device 10 held by the worker for which the value indicated by the biological information is in a dangerous range from the destinations of sending a rescue request.

The pairing management unit 115 of the terminal device 10a cancels pairing with the associated biosensor device 20 and establishes pairing with another biosensor device 20 connectable with the terminal device 10a by near field communication. The process is performed for all the biosensor devices 20 detected. When the biological information acquired from all the biosensor devices 20 detected has been evaluated, the terminal device 10a and the detected biosensor devices 20 return the pairing devices to the original state.

Figure 8:
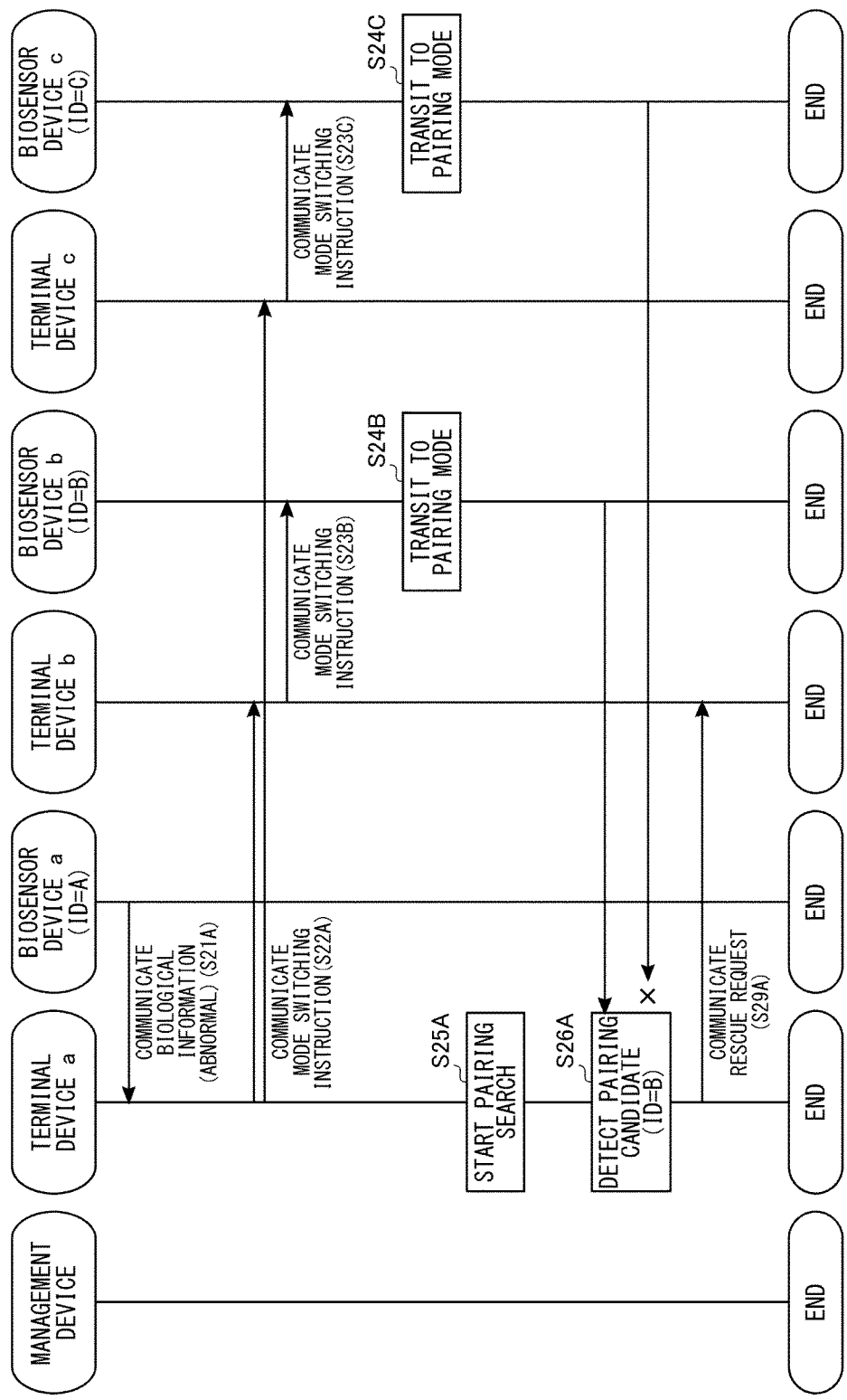
FIG. 8 is a flowchart illustrating a method of requesting a rescue by using the dangerous operation support system according to a variation to Embodiment 1.

FIG. 8 is a flowchart illustrating a method of requesting a rescue by using the dangerous operation support system 1 according to a variation to Embodiment 1. The processes through step S26A of the flowchart of FIG. 8 are the same as those of the flowchart of FIG. 7. In the variation, the storage unit 12 of the terminal device 10 is also provided with a device information storage unit, like the storage unit 32 of the management device 30.

In the variation, the terminal device 10a directly sends a rescue request to worker B without being mediated by the command center 3. In other words, the rescue request communicating unit 118 of the terminal device 10a communicates a rescue request to the terminal device 10b held by worker B by business wireless communication, based on the result of pairing search (S29A). Since the terminal device 10b is within the range covered by radio waves for near field communication, the terminal device 10b may communicate a rescue request by near field communication instead of business wireless communication. If a display unit is provided in the biosensor device 20, the rescue request communicating unit 118 may communicate a rescue request to the biosensor device 20b by near field communication.

If multiple biosensor devices 20 connectable to the terminal device 10a by near field communication are detected as a result of the pairing search in step S26A above, the communication destination determination unit 116 determines the terminal device 10 held by the worker wearing the biosensor device 20 (one of the multiple biosensor devices 20 that are connectable) with the highest radio field intensity as the destination of sending a rescue request. A rescue request may be sent to multiple destinations. In this case, the communication destination determination unit 116 identifies a preset number of biosensor devices in the descending order of radio field intensity, from the multiple connectable biosensor devices 20. The communication destination determination unit 116 determines multiple terminal devices 10 held by multiple workers wearing the identified biosensor devices 20 as the destination of sending a rescue request.

Of the pairing candidates detected in step S26A above, the communication destination determination unit 116 only defines the terminal device 10 held by the worker wearing the biosensor device 20 having its identification information stored in the device information storage unit as the candidate of sending a rescue request. In other words, the rescue request communicating unit 118 excludes the terminal device 10a held by a worker other the workers belonging to the same team from the targets of communicating a rescue request. If the biosensor device 20 as detected is of the same type as the biosensor device 20 of the requesting worker but is worn by a worker of another team, the terminal device 10 held by the worker wearing the detected biosensor device 20 is excluded from the destinations of sending a rescue request.

As described above, according to Embodiment 1, a dangerous state of a worker can be made known to nearby workers smoothly by identifying the nearby worker using a pairing search in near field communication. By detecting the radio field intensity in near field communication, a worker estimated to be closest to the worker in the dangerous state can be identified. A worker estimated to be closest can be identified even if the worker is operating in a scene not covered by GPS waves.

Embodiment 2

Figure 9:
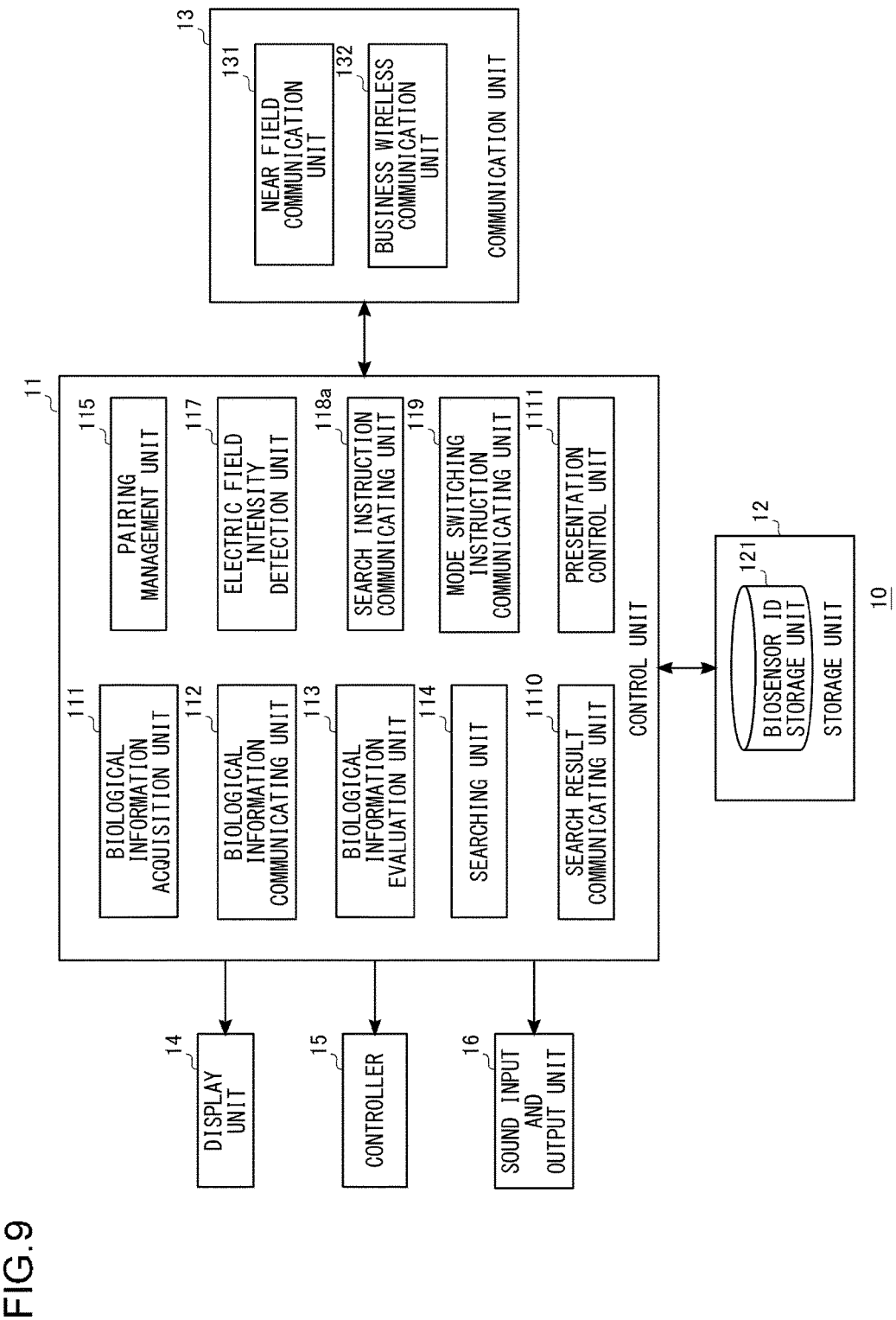
FIG. 9 shows the configuration of the terminal device according to Embodiment 2.

FIG. 9 shows the configuration of the terminal device 10 according to Embodiment 2. The control unit 11 of the terminal device 10 according to Embodiment 2 includes a biological information acquisition unit 111, a biological information communicating unit 112, a biological information evaluation unit 113, a searching unit 114, a pairing management unit 115, an electric field detection unit 117, a search instruction communicating unit 118a, a mode switching instruction communicating unit 119, a search result communicating unit 1110, and a presentation control unit 1111. The features other than the control unit 11 are identical to the features of the management device 30 according to Embodiment 1 shown in FIG. 3.

Figure 10:
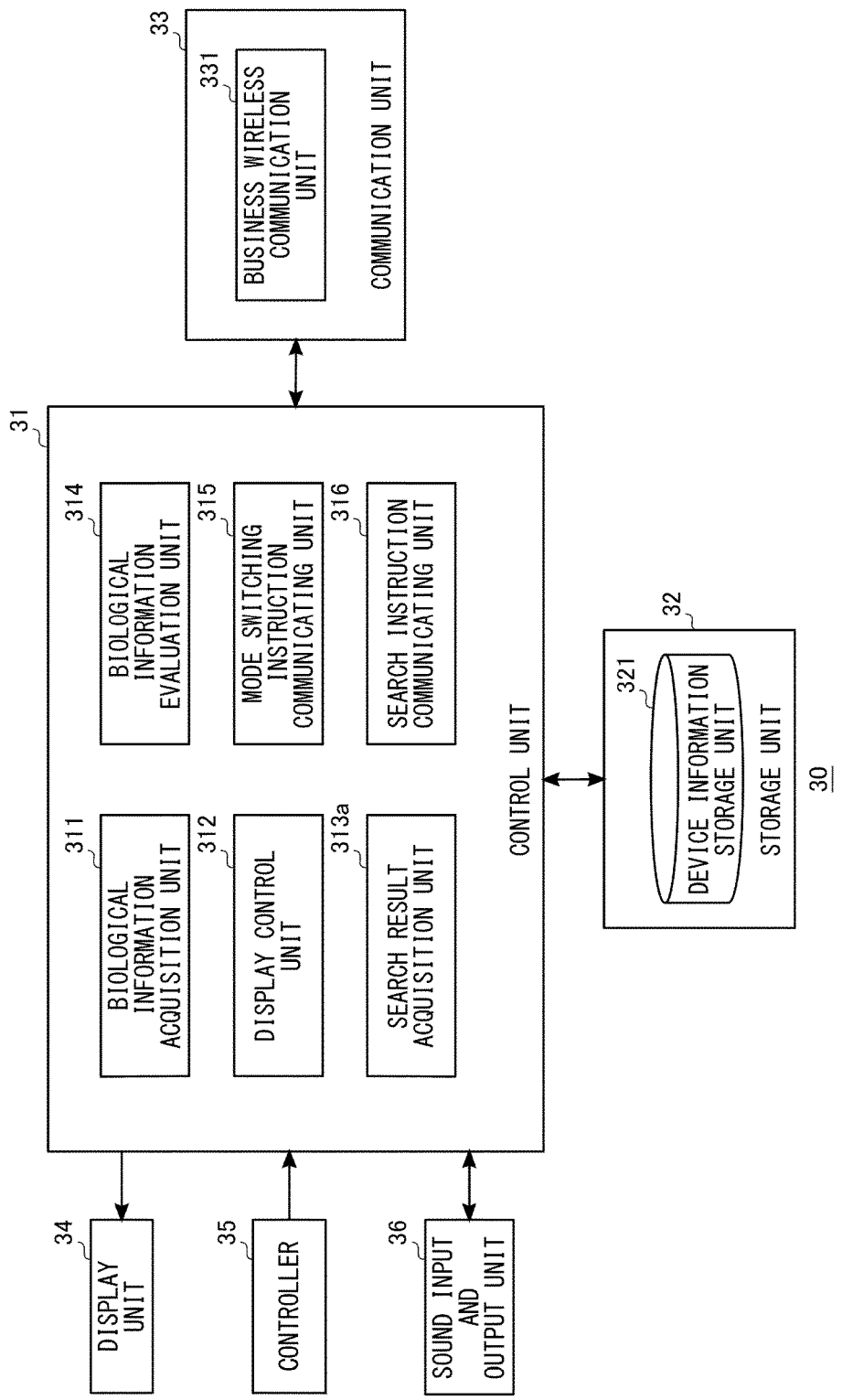
FIG. 10 shows the configuration of the management device according to Embodiment 2.

FIG. 10 shows the configuration of the management device 30 according to Embodiment 2. The control unit 31 of the management device 30 according to Embodiment 2 includes a biological information acquisition unit 311, a display control unit 312, a search result acquisition unit 313a, a biological information evaluation unit 314, a mode switching instruction communicating unit 315, and a search instruction communicating unit 316. The features other than the control unit 31 are identical to the features of the management device 30 according to Embodiment 1 shown in FIG. 4.

Figure 11:
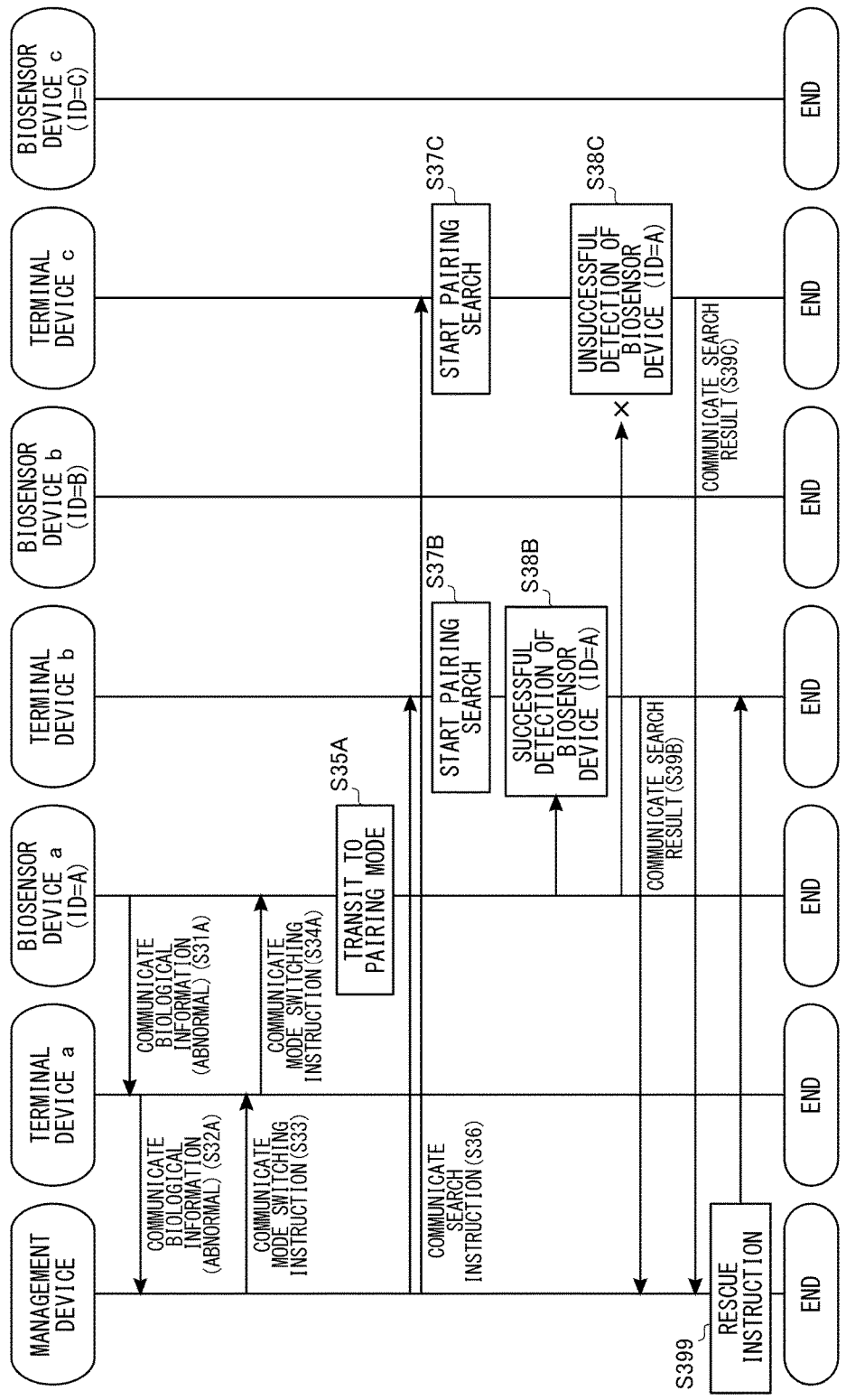
FIG. 11 is a flowchart illustrating a method of requesting a rescue by using the dangerous operation support system according to Embodiment 2.

FIG. 11 is a flowchart illustrating a method of requesting a rescue by using the dangerous operation support system 1 according to Embodiment 2. The biological information acquisition unit 211 of the biosensor device 20a acquires biological information on worker A from the sensor unit 24. The biological information communicating unit 212 communicates the acquired biological information to the terminal device 10a by near field communication (S31A).

The biological information acquisition unit 111 of the terminal device 10a paired with the biosensor device 20a acquires the biological information on worker A from the biosensor device 20a by near field communication. The biological information communicating unit 112 communicates the biological information on worker A to the management device 30 of the command center 3 by business wireless communication (S32A). The biological information acquisition unit 311 of the management device 30 acquires the biological information on worker A from the terminal device 10a by business wireless communication. The biological information evaluation unit 314 determines whether the acquired biological information on worker A is normal.

If the biological information on worker A is determined to be abnormal, the mode switching instruction communicating unit 315 of the management device 30 communicates a mode switching instruction to the terminal device 10a by business wireless communication to direct the terminal device 10a to switch the biosensor device 20a from the normal mode to the pairing mode (S33). When the mode switching instruction communicating unit 119 of the terminal device 10a acquires the mode switching instruction from the management device 30 by business wireless communication, the mode switching instruction communicating unit 119 communicates the mode switching instruction to the biosensor device 20a by near field communication (S34A). When the mode control unit 213 of the biosensor device 20a acquires the mode switching instruction from the terminal device 10a by near field communication, the mode control unit 213 causes the biosensor device 20a to make a transition from the normal mode to the pairing mode (S35A). If the devices are configured to return a response to a pairing search from other devices in the normal mode as well, the processes in steps S33, S34A, and S35A are omitted.

After the biosensor device 20a has made a transition to the pairing mode, the search instruction communicating unit 316 of the management device 30 communicates a search instruction to the terminal devices 10b and 10c worn by workers B and C, respectively, by business wireless communication, to direct the terminal devices 10b and 10c to initiate a pairing search for the biosensor device 10a worn by worker A by near field communication (S36). The identification information (ID=A) of the biosensor device 20a searched for is appended to the search instruction.

Upon acquiring the search instruction from the management device 30, the searching unit 114 of the terminal device 10b starts a pairing search to search for a device connectable by near field communication (S37B). The terminal device 10b held by worker B is at a distance capable of near field communication with the biosensor device 20a, the biosensor device 20a searched for is detected as a pairing candidate (S38B).

The presentation control unit 1111 causes the display unit 14 to display that worker A in a dangerous state is nearby. This allows worker B to recognize that worker A in need of a rescue is within the range covered by radio waves for near field communication. The presentation control unit 1111 may cause the sound input and output unit 16 to output a sound to alarm that worker A in a dangerous state is nearby. The search result communicating unit 1110 communicates a search result including a message indicating that the biosensor device 20a searched for is successfully detected to the management device 30 by business wireless communication (S39B).

As in the terminal device 10a, the searching unit 114 of the terminal device 10c also starts a pairing search for a device connectable by near field communication, upon acquiring a search instruction from the management device 30 (S37C). Since the terminal device 10c held by worker C is not within the range covered by radio waves for near field communication with the biosensor device 20a, the biosensor device 20a searched for is not detected as a pairing candidate (S38C). The search result communicating unit 1110 communicates a search result, including a message indicating the failure to detect the biosensor device 20a searched for, to the management device 30 by business wireless communication (S39C).

The search result acquisition unit 313a of the management device 30 acquires the search result from the terminal devices 10b and 10c by business wireless communication. The display control unit 312 causes the display unit 34 to display that worker B is near worker A in a dangerous state. The display control unit 312 also acquires the device information on worker B from the device information storage unit 321 and causes the display unit 34 to display the acquired information. The commander viewing the screen on which these items of information are shown tells worker B that worker A in a dangerous state is nearby and to rescue worker A. For example, the commander sends sound from the sound input and output unit 16 to the terminal device 10b by business wireless communication (S399) to give the instruction.

In step S38B above, the electric field detection unit 117 of the terminal device 10b may detect the radio field intensity of a response signal transmitted from the biosensor device 20a detected by the pairing search. The search result communicating unit 1110 communicates a search result including a message indicating that the biosensor device 20a worn by worker A is successfully detected and the detected radio field intensity to the management device 30 by business wireless communication. By reporting a search result including the radio field intensity to the command center 3 in a case the biosensor device 20a worn by worker A is detected by multiple terminal devices 10, the commander can know which worker is closest to worker A by referring to the radio field intensity.

After step S38B above, the pairing management unit 115 of the terminal device 10b may establish pairing with the biosensor device 20a worn by worker A detected. If the system is designed to enable only one-to-one pairing, the terminal device 10b and the biosensor devices 20a detected by the pairing search temporarily cancel the pairing established previously and establish pairing between the terminal device 10b and the biosensor device 20a.

The biological information acquisition unit 111 of the terminal device 10b acquires biological information from the biosensor device 20a newly paired with the terminal device 10b. The presentation control unit 1111 causes the display unit 14 to display the acquired biological information and/or causes the sound input and output unit 16 to output sound. For example, the numerical value of the acquired biological information may be read out by speech synthesis. Worker B can know how dangerous worker A is by referring to the presented biological information and use it to build a rescue plan.

Figure 12:
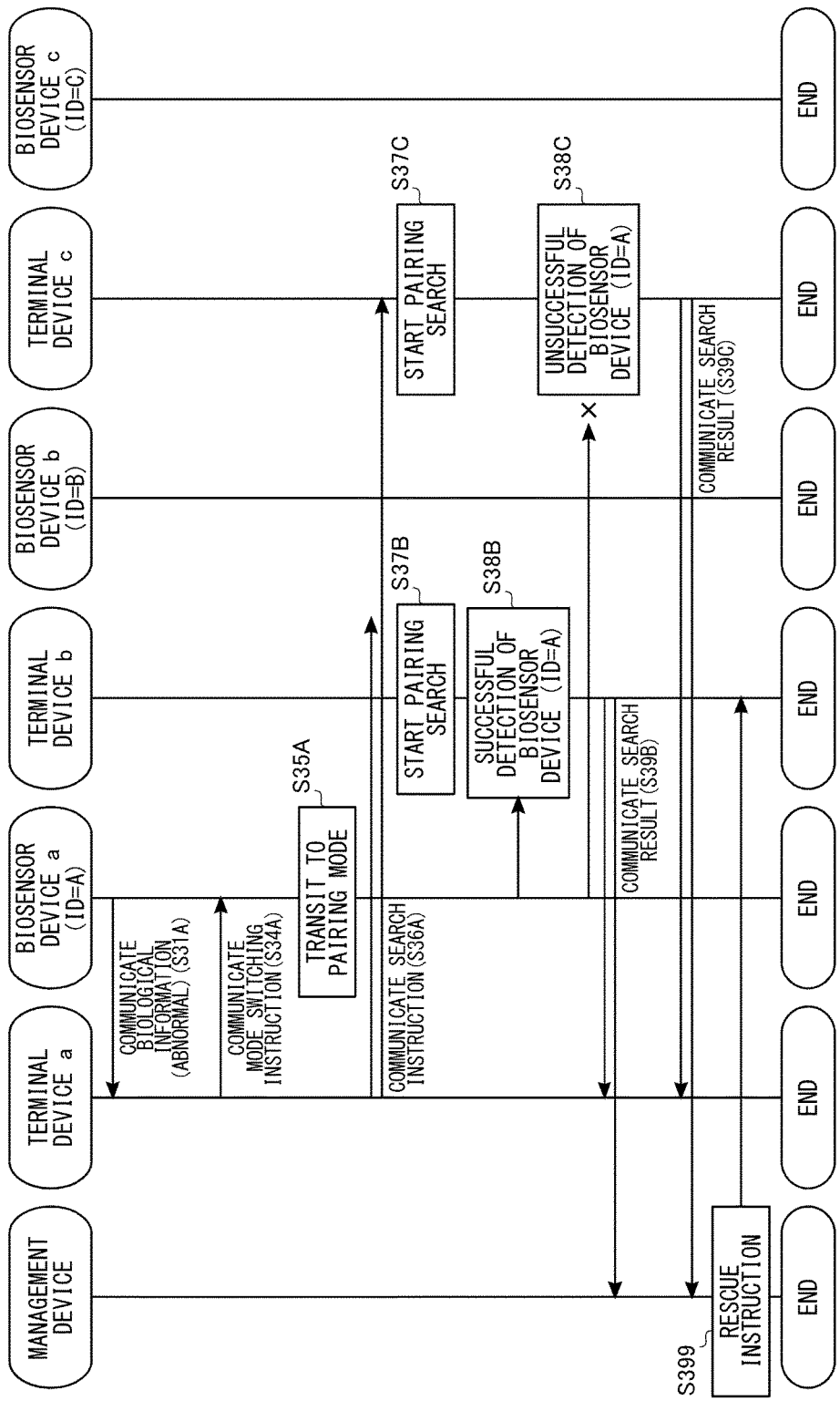
FIG. 12 is a flowchart illustrating a method of requesting a rescue by using the dangerous operation support system according to a variation to Embodiment 2.

FIG. 12 is a flowchart illustrating a method of requesting a rescue by using the dangerous operation support system 1 according to a variation to Embodiment 1. The biological information acquisition unit 211 of the biosensor device 20a acquires biological information on worker A from the sensor unit 24. The biological information communicating unit 212 communicates the acquired biological information to the terminal device 10a by near field communication (S31A).

The biological information acquisition unit 111 of the terminal device 10*a* paired with the biosensor device 20*a* acquires the biological information on worker A from the biosensor device 20*a* by near field communication. The biological information evaluation unit 113 determines whether the acquired biological information on worker A is normal. If the biological information on worker A is determined to be abnormal, the mode switching instruction communicating unit 119 communicates a mode switching instruction to the biosensor device 20*a* by business wireless communication to direct the biosensor device 20*a* to switch from the normal mode to the pairing mode (S34A). When the mode control unit 213 of the biosensor device 20*a* acquires the mode switching instruction from the terminal device 10*a* by near field communication, the mode control unit 213 causes the biosensor device 20*a* to make a transition from the normal mode to the pairing mode (S35A). If the devices are configured to return a response to a pairing search from other devices in the normal mode as well, the processes in steps S34A and S35A are omitted.

The subsequent processes are identical the processes following steps S35B and S35C in the flowchart of FIG. 11. In the variation, the search result communicating unit 1110 of the terminal devices 10*b* and 10*c* may communicate the search result to both of the requesting terminal device 10*a* and the management device 30 by business wireless communication (S39B, S39C).

As described above, according to Embodiment 2, a dangerous state of a worker can be made known to a nearby worker smoothly by identifying the nearby worker using a pairing search in near field communication. Since multiple terminal devices 10 conduct a pairing search for the biosensor device 20 worn by the worker in a dangerous state, the redundancy is high. Even if a trouble occurs in the near field communication unit 131 of one of the terminal devices 10, the worker holding another terminal device 10 detecting the biosensor device 20 can come to a rescue.

Described above is an explanation based on an exemplary embodiment. The embodiment is intended to be illustrative only and it will be obvious to those skilled in the art that various modifications to constituting elements and processes could be developed and that such modifications are also within the scope of the present invention.

In Embodiment 1, the searching unit 114 of the terminal device 10*a* searches for a device connectable in near field communication when the biological information on worker A detected by the biosensor device 20*a* is abnormal. A trigger other than abnormality in biological information can start a search so long as the trigger indicates abnormality in worker A undertaking a dangerous operation. For example, a heat sensor or a smoke sensor may be provided in the terminal device 10 held by worker A and, if it is estimated that worker A falls to the floor by referring to the output values from the sensor, a search may be started. A search may be alternatively started when worker A presses down a rescue request button of the controller 15 of the terminal device 10*a*.

In Embodiments 1 and 2, the biosensor device 20 is searched for in a pairing search as a slave module in near field communication. The terminal devices 10 held by other workers may also be searched for in the pairing search. Since the biosensor device 20 is less likely to be removed from the body of a worker than the terminal device 10, it would be appropriate to use the result of search for the biosensor device 20 in preference to the result of search for the terminal device 10, if the results differ.

The biosensor device 20 according to Embodiments 1 and 2 is an example of communication terminal device on which the near field communication unit 131 is mounted and on which the business wireless communication unit 132 or a cell phone communication unit is not mounted. Therefore, an accessory device such as a headset that supports Bluetooth (registered trademark) may be used in place of the biosensor device 20.

What is claimed is:

1. A communication terminal device comprising:
   a second communication unit that communicates with a second communication terminal device by using a second communication scheme capable of communication over a longer distance than a first communication scheme; and
   a search instruction communicating unit that communicates a search instruction to the second communication terminal device via the second communication unit, the search instruction including an identifier identifying a first communication terminal device that communicates by using the first communication scheme, and instructing the second communication terminal device to search for the first communication terminal device identified by the identifier by using the first communication scheme.

2. The communication terminal device according to claim 1, further comprising:
   a first communication unit that communicates with the first communication terminal device by using the first communication scheme; and
   a mode switching instruction communicating unit that communicates, before the search instruction communicating unit communicates a search instruction to the second communication terminal device, a mode switching instruction to the first communication terminal device via the first communication unit, the mode switching instruction instructing the first communication terminal device to switch from a mode in which the first communication terminal device does not respond to a search from other devices to a mode in which the first communication terminal device responds to a search from other devices.

* * * * *